United States Patent [19]

Kuy

[11] 4,355,020

[45] Oct. 19, 1982

[54] THIXOTROPIC ALUMINUM HYDROXIDE CHLORIDE AND MEDICAL AND OTHER APPLICATIONS THEREOF

[76] Inventor: Bert Kuy, Holzestrasse 28, Zurich 8042, Switzerland

[21] Appl. No.: 169,479

[22] Filed: Jul. 15, 1980

Related U.S. Application Data

[63] Continuation-in-part of Ser. No. 957,333, Nov. 3, 1978, abandoned.

[30] Foreign Application Priority Data

Nov. 12, 1977 [GB] United Kingdom ............... 47179/77

[51] Int. Cl.$^3$ ..................... A61K 9/70; A61K 33/08; A61K 7/38; A61K 31/79
[52] U.S. Cl. ........................................ 424/28; 424/20; 424/68; 424/80; 424/83; 424/157
[58] Field of Search ..................... 424/28, 20, 68, 154, 424/157, 80, 83

[56] References Cited

U.S. PATENT DOCUMENTS

| | | | |
|---|---|---|---|
| 2,492,085 | 12/1949 | Andersen | 424/154 |
| 3,359,169 | 12/1967 | Slater et al. | 424/157 |
| 3,630,670 | 12/1971 | Bell et al. | 23/143 |
| 3,638,327 | 2/1972 | Levy et al. | 424/68 |
| 3,655,329 | 4/1972 | Shih et al. | 424/157 |
| 3,739,062 | 6/1973 | Bargotti | 423/625 |
| 3,813,466 | 5/1974 | Andersen | 424/28 |
| 3,886,125 | 5/1975 | Chromecek | 424/47 |

FOREIGN PATENT DOCUMENTS

1174648 12/1969 United Kingdom .

OTHER PUBLICATIONS

Chem. Abst. 78 128,444(a) (1973) Pelz and Co.
Baker et al. "J. of Catalysis" 33, 265–278 (1974).
Bye et al. J. Appl. Chem. Biotechnol 24, 633–637 (1974).
Chem. Abst. 75, 78704(a) (1971), Nagumo et al.
Chem. Abst. 75, 29412(v) (1971), Chesworth.

*Primary Examiner*—Douglas W. Robinson
*Attorney, Agent, or Firm*—Browdy & Neimark

[57] ABSTRACT

The present invention relates to novel compositions of matter and their use in medicine, in agricultural applications, and in cosmetics. The compositions are based on a thixotropic aluminum hydroxide chloride which has an atomic ratio of aluminum to chlorine of from 5:1 to 6:1, and which is the chlorination product of pseudoboehmite which aluminum hydroxide chloride is in a concentration in water of from about 2 to about 20 weight percent. For medical topical application a suitable carrier is impregnated with such thixotropic microcrystalline aluminum hydroxide chloride.

17 Claims, No Drawings

THIXOTROPIC ALUMINUM HYDROXIDE CHLORIDE AND MEDICAL AND OTHER APPLICATIONS THEREOF

CROSS-REFERENCE TO RELATED APPLICATIONS

The present invention is a continuation-in-part of U.S. application Ser. No. 957,333, filed Nov. 3, 1978, now abandoned, the entire contents of which are hereby incorporated by reference.

FIELD OF THE INVENTION

The present invention relates to a novel composition of matter and its method of use in medicine, cosmetics, in physical therapy, and in agricultural applications. The novel composition of matter is adapted to provide effective healing and soothing effects in the form of bandages, as hot and cold compresses and for similar uses.

BACKGROUND OF THE INVENTION

Aluminum hydroxides and aluminum hydroxyoxides are well known compounds and well established in industrial usage. These compounds can appear in various crystalline forms which can have a significant effect on their properties. Examples of such various forms are known under the names of hydrargillite, bayerite, nordstrandite, boehmite, diaspore, pseudoboehmite, etc.

Basic aluminum chlorides, or aluminum chlorhydroxides as they are sometimes termed, are also well known compounds of the formula $Al_2(OH)_{6-n}Cl_n (n=1$ to $5)$. Such compounds have been widely used in deodorant, antiperspirant and fungicidal preparations.

Various attempts have been made to provide aluminum chloride hydrates of differing structures in order to improve their properties for various applications. Note, for example, U.S. Pat. No. 3,655,329 to Shih et al. A common problem with such known aluminum chlorhydroxide compounds is that they are all soluble in water.

SUMMARY OF THE INVENTION

Accordingly, it is an object of the present invention to eliminate the deficiencies of the prior art, such as those set out hereinabove.

It is another object of the present invention to provide a composition based on a water-insoluble aluminum hydroxide chloride compound which has thixotropic properties.

It is yet another object of the present invention to provide medical applications, such as bandages, which include such thixotropic aluminum hydroxide chloride compounds.

It is still another object of the present invention to provide a method of use of such thixotropic aluminum hydroxide chloride compounds in medical, cosmetic, and agricultural applications.

It is a further object of the present invention to provide an aluminum hydroxide chloride composition which can be mechanically applied by rolling, brushing and spraying, and also by dipping in any quantity required on or in a suitable carrier.

It is still a further object of the present invention to provide an aluminum hydroxide chloride composition which can be distributed easily in minimum or maximum quantities in an equal and homogeneous manner without flowing off and has a strong adhesion on porous, homogeneous or lipoid surfaces of materials like textiles, synthetic and natural materials.

It is yet a further object of the present invention to provide an aluminum hydroxide chloride composition to which further additives can be added without the need to use an emulsifier.

It is another object of the present invention to provide an aluminum hydroxide chloride composition which is stable over a long period of time and can be brought into any consistency required by applying pressure or any mechanical forces like vacuum.

It is yet another object of the present invention to provide an aluminum hydroxide chloride composition which is reversible in binding high volumes of moisture or water, and which is insoluble in water and difficultly washed off, resulting in an increased effect and lack of toxicity in topical administration. The novel composition has osmotic properties which remain unchanged and belong to the strongest among the known aluminum compounds. Furthermore, the novel composition shows a long time activity at low dosages and has a reversible adhesive power and therefore reactivates itself continuously effectively.

Still other objects, features and attendant advantages of the present invention will become apparent to those skilled in the art from a reading of the following detailed description of embodiments in accordance therewith.

DESCRIPTION OF PREFERRED EMBODIMENTS

The active ingredient of the composition according to the present invention is a colloidal system of an aluminum hydroxide chloride having an atomic ratio of aluminum to chloride in the range of 5:1 to 7:1, and preferably 5:1 to 6:1. Such a composition is prepared by the reaction of the alumina hydrogel pseudoboehmite with an appropriate amount of hydrochloric acid. Pseudoboehmite per se is of course well known, as exemplified by U.S. Pat. Nos. 3,630,670 and 3,739,062, as well as the article by Baker, B. R. et al, "Water Content of Pseudoboehmite: A New Model for Structure", *Journal of Catalysis*, 33, 265–278 (1974). A commercial example of pseudoboehmite is the product called "aluminum hydroxide E.P." sold by Gebr. Giulini G.m.b.H. of Ludwigshafen-am-Rhein, Germany. It is critical that the alumina hydrogel material used as the starting material for the manufacture of the composition of the present invention be pseudoboehmite in order that a thixotropic aluminum hydroxide chloride gel may be obtained. When pseudoboehmite is used as the starting material, the aluminum hydroxide chloride of the present invention forms a gel with water. Even at great rates of dilution no clear solution is formed but an opaque appearance remains. This clearly indicates that it is a gel in which the active substance is present in colloidal form and these colloids are tied into a three-dimensional space with the inclusion of water. This explains the thixotropic behavior of this gel.

In producing the product of the present invention, 1–2 normal HCl is used in the calculated stoichiometric amount to obtain a composition having an atomic ratio of aluminum to chlorine in the range of 5:1 to 6:1. The pseudoboehmite used in the reaction is preferably in the form of a paste containing 10–15% of aluminum calculated as $Al_2O_3$. Pseudoboehmite is commercially available as a powder with an amount of aluminum calculated in the form of $Al_2O_3$ of 70%.

It is believed that the substance of the present invention may be represented by the formula $[Al(OH)_3]_xAl(OH)_2Cl$ where x varies between 4 and 5. The thixotropic active material of the present invention will be referred in the followng specification and claims as "aluminum hydroxide chloride".

The pH of the thixotropic composition varies between about 3.5 and about 5, and generally between 3.5 and 3.8.

The novel composition may optionally contain additional ingredients according to the specific uses of the composition. The additional ingredients may be, for example, fatty substances, such as lanolin, oleic acid, fatty alcohols, stearic acid, or the like, collagen, polyalkylene, disinfectants, fungicides, bacteriostats, bactericides, fungistats, antimycotics, tartaric acid and glycerol. It is very important to be able to incorporate fatty substances such as lanolin, $C_8$–$C_{22}$ fatty acids, $C_8$–$C_{20}$ fatty alcohols, or the like, into the present invention, as it has generally been very difficult to incorporate such fatty substances into a system which contains a very high content of aluminum compound of this type.

The thixotropic aluminum hydroxide chloride of the present invention may advantageously be used to impregnate a suitable inert carrier, such as cellulosic material (paper, cellulose, cotton wool, cotton, etc.) or any other suitable carrier, such as foams, fabrics, mixed fabrics, non-woven fabrics, gauze and the like. Even hydrophobic polymeric foams such as polyurethane foam may be suitably impregnated by the thixotropic compound of the present invention.

A suitable quantity of the active ingredient is used to imbue or impregnate the carrier, the quantity of the active ingredient being such as to provide as high an effective quantity of the active material as can be supported by the carrier. Representative values of such quantities are from 10 to 35 g per 100 cm$^2$ of a material such as plastic foam or gauze.

The above ingredient, i.e. the thixotropic aluminum hydroxide chloride exerts an astrigent action on human skin, without causing undue irritation. It exerts a certain acid binding activity, and due to its inherent pH of about 3.5 to pH 5 it is well suffered by human skin. Into the above thixotropic system there may be readily incorporated substances such as 3–5% lanolin; which latter had generally previously been obtained as a stable system with aqueous ingredients only in conjunction with other constituents such as surface active agents or the like. It exerts an antiphlogistic and soothing action.

The aluminum hydroxide chloride in accordance with the present invention exhibits thixotropic properties within the range of about 2 to about 20% concentration in water. It is preferably used at a concentration of about 10%. At such concentrations the aluminum hydroxide chloride in water forms a gel which can be easily liquefied by application of mechanical forces, such as by shaking, brushing or the like. The viscosity decreases thereby about 100 fold, from values in the range of 10,000 cps to about 100 cps. When left to stand it reverts again to the high viscosity.

The thixotropic substance can be applied directly to the skin or mucosa for medical uses. It can also be provided in conjunction with bandages which serve as carrier of the active ingredient. The water of the compositions evaporates in a gradual manner, and there remains a coating of aluminum hydroxide chloride, which allows the skin to breathe and which maintains its activity over a prolonged period of time.

The new compositions of matter are generally used externally and thus very little of the essentially insoluble materials is adsorbed, if any at all. Toxicity tests indicate that the application of oral dosages of about 5 g/kg weight of the thixotropic aluminum chloride to rats does not result in toxic effects.

The bandage may be backed with a layer such as aluminum foil and can be used, for example, as a hot compress of prolonged useful duration of application.

When the active ingredient is used in conjunction with a suitable carrier, the carrier is impregnated with the active ingredient either by pressure, under reduced pressure, by brushing, coating or spraying. There is obtained a substantially homogeneous product carrying a predetermined quantity of active material per unit area.

The thixotropic properties of the aluminum hydroxide chloride of the present invention permits exact dosages. In order to coat foam, non-woven material and paper rolls with the described gel on a production scale, or to place the gel thereon, the material, for example of a width of 2 meters, is unrolled from large rolls onto coating machines with a roller track of 10 meters in length. The aluminum hydroxide chloride flows out of a container and is maintained in liquid form by its own weight. The aluminum hydroxide chloride flows onto the running material and becomes distributed evenly to the entire 2 m width, proportionally with the speed of the material moving therethrough. The exact dosage may be determined by means of a distributor bar. For example, a 4 mm thick layer of aluminum hydroxide chloride on the foam, non-woven material, or paper substrate may be obtained and is moved along with the material.

To impregnate the material, particularly when it is a porous material, such as a foam, the material along with the layer of aluminum hydroxide chloride, is pressed by rollers at the end of the roller track. Upon release of the pressure, a suction is created which sucks the aluminum hydroxide chloride material into the capillaries of the foam material permitting the even penetration of an exactly measured amount of aluminum hydroxide chloride into the pores of the foam material, i.e. the aluminum hydroxide chloride gel is not pressed in but is soaked up. This makes it possible to fully utilize the empty spaces in the foam material and to measure the gel according to the requirement of 300 g/m$^2$.

Only the thixotropic properties of the aluminum hydroxide chloride gel of the present invention permits this type of fabrication. In order to obtain a coating with a concentration of 300 g/m$^2$ using a prior art aluminum hydroxide chloride material which is water-soluble, so much emulsifier would have to be added that the pores of the foam material would be filled with ineffective and interfering substances. Furthermore, it is problematic whether non-adhesive components can be evenly distributed in thicknesses of more than 1 mm on a coating machine as the material would simply flow off and not be maintained in greater thicknesses as with the thixotropic material of the present invention. This would mean that the desired quantity could not be applied in one operation.

The thixotropic aluminum hydroxide chloride gel of the present invention is an ideal composition for many application purposes including those discussed hereinabove and guarantees fast and effective coating, spraying, as well as absorption and dosage in maximal quantity with a minimum of effort. None of the prior art similar aluminum composition can be worked according to the process described. Such compositions do neither permit application in the desired amounts on the required roller tracks, nor can they be absorbed in the most effective quantity by pressure and the suction caused thereby. With a liquid viscosity, the volume will remain limited since the quantity will be absorbed only to that extent (based on the flexibility of the foam material or other carrier) which is permitted by the action of the dripping or emptying action of the viscosity. With a firmer viscosity, larger quantities can be applied by coating but an absorption into the capillaries of the carrier is made more difficult and an even distribution is not achieved.

The viscosity is variable with the thixotropic aluminum hydroxide chloride gel of the present invention. During coating it is a firm gel maintained in a fluid state solely by its own weight and the movement of the carrier and is applied in the desired thickness by means of the distributor, becoming firm again because of the quiet movement on the roller track. This is the prerequisite for the roller press to force the desired amount through the foam material. Next the aluminum hydroxide chloride is pressed in a completely liquid state through the foam material and when the pressure is released, the foam material returns to its previous form. The suction caused by this action pulls the desired amount of aluminum hydroxide chloride into the hollow spaces. This results in an even distribution of the substance.

It has been difficult in the past to impregnate hydrophobic materials, such as hydrophobic polyurethane foam with water-soluble material. They do not obtain an even wetting. However, the method described hereinabove permits a fast and effective soaking of polyurethane foam materials of large widths and indefinite lengths in a simple and cost-effective process. Only a thixotropic material will obtain these advantages.

When less porous carriers are used, no pressure by the rollers is applied as this would only serve to push off the gel or to wipe it off of the carrier. A layer of from 2 to 3 mm of gel is left to remain on the carrier material without being absorbed into the hollow spaces. At the end of the roller track, the high viscosity gel is provided with a protective paper cover.

Carriers impregnated with the aluminum hydroxide chloride gel of the present invention my be used in medical application, for example, in bandages. The aluminum hydroxide chloride gel of the present invention is easily tolerated in medical applications in its pure form as well as in connection with carriers, such as polyurethane. Especially in long-lasting therapy or large scale skin defects no diffusion of the material occurs. Only because of the insolubility in water of the thixotropic aluminum hydroxide chloride gel of the present invention can compresses impregnated with this material be utilized for such therapy. Blood and urine samples do not show any change in the electrolytic balance. Similar results cannot be expected with water soluble aluminum compounds such as those of the prior art.

The aluminum hydroxide chloride gel of the present invention is also useful for the cleaning of wounds and is very effective because of its protein splitting antibacterial properties. It sticks to the surface and loosens the necrotic tissue. Thanks to its purity it can remain in the wound and it does not prevent granulation. Such effects could not be expected from other aluminum compounds which are not water-insoluble and which do not have the adhesion properties of the composition of the present invention.

A compress filled with the thixotropic aluminum hydroxide chloride gel of the present invention can be utilized therapeutically without the appearance of skin changes by day and by night without time restriction.

The thixotropic aluminum hydroxide chloride gel of the present invention can also be advantageously used in agricultural applications for protection against afflictions by various pests, and especially by fungi. Extensive tests have shown that the thixotropic material can be applied directly to various types of agricultural products such as grains, maize, barley, and the like, and to various types of fruit, etc. There is formed a thin coating which adheres well to the surface of the treated agricultural product and this thin film constitutes a protective barrier against various afflictions, and especially against fungal attack. The prevention of fungal growth prevents the production of aflotoxins which are presently considered to be a serious health hazard. When subjected to rain or to irrigation, the protective coating is not washed off and it retains its efficacy over a prolonged period of time.

Laboratory tests were carried out with various types of fruit, such as strawberries, peaches, citrus fruit, cherries, grapes, pears and apples. Tests were carried out with vegetables such as cucumbers, eggplants, potatoes and tomatoes. These were sprayed or brushed with a colloidal suspension of the thixotropic aluminum hydroxide chloride containing a small quantity of a nonionic surfactant. The resulting non-poisonous and harmless coating substantially reduced fungal attack and also substantially reduced oxidative effects. Formation of spots was retarded and evaporation of water was substantially reduced. For example, citrus fruits retained their fresh appearance and lost weight at a substantially reduced rate compared with similar untreated fruit. Meat and meat products, such as meat, sausages, smoked meat and the like can be protected against fungal attack and against weight loss by a thin protectives coating of this type. Generally there were used colloidal thixotropic compositions containing from about 3 to 10% by weight of the aluminum hydroxide chloride.

Tests were carried out with corn and with maize and laboratory tests proved a substantial reduction of fungal affliction of the treated samples. Furthermore, it was found that the treated corn dries quickly, its shrinkage is reduced and there is a decreased formation of dust. There is obtained a substantially uniform surface film which shows a good adherence and which is very little affected by irrigation or by rain. The active ingredient is characterized by its very low solubility, and there is practically no diffusion into the treated product. Due to its nature, the active ingredient is very stable.

Other and further features of the invention will become apparent hereinafter from the examples, which are to be considered in a non-limitative manner.

EXAMPLE 1

The pseudoboehmite used for the production of the aluminum hydroxide chloride of the present invention may be commercially obtained or produced by a process such as that of U.S. Pat. No. 3,630,670. One example of a method of making pseudoboehmite is as follows.

A sodium aluminate solution at about 40°–50° C. is added to a dilute aluminum sulfate solution (about 6°

Be, 1.2% $Al_2O_3$) at 25° C. and with intensive agitation. The caustic molar ratio of the sodium aluminate solution is between 1.6 and 2.0, advantageously about 1.8.

The precipitation is terminated at pH 10.0 and after stirring for 1 hour the suspension is filtered on a filter press. The filter cake is washed, dried on a drier and ground to a fine powder. The product has an $Al_2O_3$ content of about 70% and corresponds in its structure to the pseudoboehmite type of aluminum hydroxide.

The pseudoboehmite obtained is converted to the aluminum hydroxide chloride used in the compositions of the present invention by reaction with hydrochloric acid under controlled conditions.

According to a preferred embodiment there is prepared a solution of 1000 liters of water containing 16 liters concentrated hydrochloric acid and into this solution there is introduced 80 kg of pseudoboehmite, corresponding to 57 kg of $Al_2O_3$. The suspension is heated gradually to 50° C. and stirred at this temperature for 10 hours. There is obtained a highly viscous transparent gel which contains a molar ratio of aluminum to chlorine of 5.5:1, which contains 10 grams aluminum hydroxide chloride per 100 grams and which is thixotropic. This is used for the preparations of the present invention.

EXAMPLE 2

A thixotropic composition was prepared by incorporating 5 g of lanolin into 100 g of the composition of Example 1. The lanolin was gradually introduced with vigorous agitation and there was added a quantity of about 0.3 g potassium chloride per 100 g of the thixotropic substance. A uniform, stable composition was obtained.

EXAMPLE 3

A thixotropic substance was prepared by incorporating about 1.0 g of micronized argentum sulfadiazine into 100 g of the composition of Example 2. There was obtained a thixotropic substance of special value in the treatment of infected wounds.

EXAMPLE 4

A thixotropic substance was prepared by incorporating 1 to 3 g by weight of PVP-iodine into 100 g of a composition of Example 1. A germicidal substance was obtained.

EXAMPLE 5

A thixotropic substance was prepared by incorporating a quantity of from 1 to 5 g of alginate into 100 g of a composition of Example 1.

EXAMPLE 6

A composition of matter was prepared by incorporating up to about 70% by weight of pulverized polymeric foam (such as polyurethane powder) into a liquefied composition according to Example 1. There was obtained a kneadable material which solidifies under refrigeration or upon evaporation of the larger part of its water content.

EXAMPLE 7

A highly porous polymeric foam (polyurethane foam) in the form of a sheet of indefinite length was impregnated by brushing with liquefied material prepared according to Example 1. The quantity used was about 30 g of the said substance per 100 cm² of said carrier. By application of pressure to the foam carrying the thixotropic material a substantially uniform distribution of the active ingredient throughout the carrier was obtained when the pressure was released after the compression of the foam. This foam can be refrigerated and used for the effective application of cold for a prolonged period of time. The active material stabilizes the polymeric material and no amines or catalysts are given off.

EXAMPLE 8

A polyurethane sheet of the type used in Example 7 was placed on a thin non-woven fabric and impregnated as set out in Example 7 by applying the thixotropic material from the open side of the foam. The non-woven fabric constitutes a suitable carrier for application on certain types of wounds.

EXAMPLE 9

Gauze was impregnated so as to provide about 20 g of the substance of Example 1 per 100 g of the gauze. The impregnation was effected by impregnation or by brushing.

EXAMPLE 10

Non-woven cellulose fabric was impregnated in a manner set out in Example 7. The quantity used was 10 g of the material of Example 1 per 100 g of the fabric.

EXAMPLE 11

A facial mask was made from a substance according to Example 6 and into which there were incorporated a small quantity of avocado juice. The mask was applied to the face in the form of a kneadable composition according to Example 6 and left in place in the form of a layer of about 4 mm for 20 minutes. Most of the fatty deposits were removed, redness of the skin decreased substantially and the skin was tightened. The skin was thereby cleaned and refreshed.

EXAMPLE 12

A composition of matter according to Example 1 was applied by means of cotton wads to the scalp and there was obtained fluffy good-looking hair and the fat glands were cleaned. The shiny appearance of the skin disappeared.

EXAMPLE 13

An impregnated sheet of Example 7 was applied to edemas and various wounds after surgery, wounds after accidents and burns of up to the third degree. There was experienced a pronounced effect of stimulation of granulation and acceleration of smooth epithelization without irritation. Pain was allayed and itching was reduced. A marked antiinflammatory effect was experienced and the healing of the wounds took place speedily and without contamination by bacteria or fungi as bacteria and fungi cannot grow on a surface coated with the active material of the present invention. The bandage does not adhere to the wound and can be readily removed when so desired, without damage to the underlying tissues.

The high water content results in a steady evaporation of water and this brings about an efficient penetration of the aluminum compound into the tissues. The rim of the wound is maintained in a soft state and the prevention of the hardening of the wound rim is one of the main effects of the novel compositions. When the bandage is removed, there do not remain any noxious or detrimental constituents which have to be removed.

The novel compositions were tested with a number of patients. Amongst these were a case of a patient with an open extensive wound of the surface of the abdomen, of about 40 cm by 5 cm. This wound did not heal during two years. The bandage was applied and changed from time to time (70 times, twice daily). At the end of the period of 35 days the wound was clean, inflammation disappeared, a smooth epithelization had taken place and this made possible transplantations of skin and the healing of the residual surface. The patient was released from the hospital after this treatment and the wound healed completely.

A patient 90 years old with spastic right arm with decubitus since about 2 years under the armpit, with no possibility of effective treatment by conventional means, was treated with a cooled bandage according to Example 10. This was changed daily during one week. After this period of time a complete healing was attained.

A patient with second degree burns on both legs was treated by the application of bandages of Example 10. These were changed thrice daily. After 6 days the wound was clean and made possible a skin transplant.

EXAMPLE 14

A patient with fractures of a leg was treated by the application of bandages according to Example 7 which were refrigerated prior to application. The bandages were changed every 30 minutes and after 4 hours the leg was free of edemas and was ready for surgery.

EXAMPLE 15

A thixotropic aluminum hydroxide chloride according to Example 1 was used for impregnation of a nonwoven fabric or special absorbent paper. The quantity applied was 3 g per unit and they were packed in individual packages of $2\frac{1}{2} \times 3''$ envelopes, which were substantially hermetic. According to a preferred embodiment some perfume is added to provide a refreshing effect.

EXAMPLE 16

A composition of matter of Example 13 was used for intimate care, such as, for example, for cleaning the anus and vulva for elimination of itching and growth of bacteria. There was obtained a refreshing effect and an antimycotic activity. The deposit on the mucosa resulted in a perceptible effect during 4 hours.

EXAMPLE 17

A composition of matter was prepared consisting of 60 parts by weight of a substance according to Example 1 and 40 parts by weight of polyurethane foam in dust form. From this substance suppositories were formed which were used for the treatment of hemorrhoids. The suppositories were frozen and applied in this form. The slow melting brings about uniform distribution of the active ingredient and this results in relief and in an improved effect.

EXAMPLE 18

An impregnated sheet according to Example 7 was used in frozen form for cryotherapy. This can be effectively used for the treatment of muscle spasms, of swellings and inflammations of the musculo-skeletal system, for the treatment of post-surgical edemas, for the treatment of phlebitis and for rheumatoid arthritis.

A patient with myositis of the left gastrocnemius muscle was treated with such an ice bandage, the duration of each being 15 minutes. After the initial analgesia, mobilization exercises were started and continued for ten minutes. After this the bandage was removed and the procedure was repeated with a fresh bandage. The therapeutic results were obtained much more quickly than with conventional methods of treatment.

EXAMPLE 19

Non-woven cotton was mixed with a composition according to Example 1. After initial drying an insole form was cut and this was applied to the bottom surface of the foot. A stocking was worn by the person, who had a history of excessive sweating (hyperhydrosis). After one day of regular activity, the foot with this insole was free of sweat, while the other foot was wet. This insole also prevented the development of fungi.

Another test was carried out with an insole of polyurethane foam impregnated by a composition according to Example 1. This was used for application under the armpit. After one day the area was dry. The other armpit was wet and an acrid smell was perceptible.

EXAMPLE 20

A composition according to Example 1 was tested in order to evaluate its activity on fruit and vegetables. A peach was cut in half, and one half was treated by the application of a thin layer of such composition. After 4 hours the treated surface was clean and free of discoloration. The other, untreated half exhibited brownish discolored area. After further 10 hours the treated area was still clear, while the untreated one was covered with fungal growth. The two halves were placed in contact with each other and left overnight. The untreated one exhibited further deterioration while the treated one remained clear.

A further test was carried out with another peach. The treated half remained free of fungal attack after 48 hours while the untreated half was badly deteriorated.

A peach was coated with a thin layer of the composition of Example 1 and placed amongst already slightly contaminated peaches. After one week the untreated fruit were completely covered with fungi whereas the treated one was quite clean.

EXAMPLE 21

A very efficient absorbent material for use in medicine and especially in general surgery and in dental practice was prepared by impregnating a suitable open pore polymeric foam, such as polyurethane foam, with a thixotropic substance according to Example 1. Excess was removed by application of pressure and the resulting material was used as absorbent. It was very efficient for the intended purpose, and could be used repeatedly after pressing out the absorbed material. It is clear that very little of the colloidal aluminum hydroxide chloride is lost from the supporting foam. In addition to the adsorptive effect a pronounced astringent effect was apparent.

EXAMPLE 22

Filter material was impregnated with a composition according to Example 1. There was obtained a very efficient filter material which can be used advantageously as filter for cigarettes, for filtering out industrial contaminants and for environmental protection.

EXAMPLE 23

The addition of tartaric acid and of glycerol to a thixotropic substance of the type defined in Example 1 results in an appreciable enhancement of the astringent properties of the composition. Even when the quantity of the aluminum hydroxide chloride is substantially reduced, an enhanced astringent effect can be obtained.

Various compositions were prepared and tested. Even compositions with as low a content of colloidal aluminum hydroxide chloride of the type defined in Example 1 as 0.1% by weight gave with 0.01% by weight tartaric acid and with 5% by weight of glycerol an astringent action 150 times stronger than that of an aluminum-acetate tartarate tested according to DAB 7.

Other compositions containing varying percentages of the above constituents were tested and corresponding results were obtained.

It is clear that the above examples are by way of illustration only and that various changes and modifications in the nature of constituents, percentage, etc. can be resorted to without departing from the scope and spirit of the invention.

What is claimed is:

1. A composition for medical application comprising thixotropic aluminum hydroxide chloride having an aluminum to chlorine ratio in the range of 5:1 to 6:1 which is the chlorination product of pseudoboehmite, and from 1-5 g per 100 g of additional ingredients selected from the group consisting of lanolin, a $C_{8-22}$ fatty acid, a $C_{8-20}$ fatty alcohol, collagen, polyalkylene, disinfectants, fungicides, bacteriostats, bactericides, fungistats, antimycotics, tartaric acid and glycerol.

2. A composition in accordance with claim 1 wherein said thixotropic aluminum hydroxide chloride is a colloidal gel of 2-20% by weight solid aluminum hydroxide chloride in water.

3. A composition in accordance with claim 1 wherein said additional ingredient is lanolin.

4. A composition in accordance with claim 1 wherein said additional ingredient is a bactericidally effective amount of bactericide.

5. An impregnated carrier comprising an inert carrier impregnated with thixotropic aluminum hydroxide chloride having an aluminum to chlorine ratio in the range of 5:1 to 6:1 which is the chlorination product of pseudoboehmite.

6. An impregnated carrier in accordance with claim 5 wherein said inert carrier is a cellulosic material.

7. An impregnated carrier in accordance with claim 5 wherein said inert carrier is a polymeric foam.

8. An impregnated carrier in accordance with claim 5 wherein said inert carrier is a fabric, mixed fabric, non-woven fabric or gauze.

9. An impregnated carrier in accordance with claim 5 wherein the impregnant further includes one or more additional ingredients selected from the group consisting of lanolin, a $C_{8-22}$ fatty acid, a $C_{8-20}$ fatty alcohol, collagen, polyalkylene, disinfectants, fungicides, bacteriostats, bactericides, fungistats, antimycotics, tartaric acid and glycerol, in an amount of from 1-5 g per 100 g of aluminum hydroxide chloride.

10. A method for exerting an astringent or adsorptive action on human skin comprising topically applying to human skin, in an amount sufficient to exert an astringent or adsorptive action, thixotropic aluminum hydroxide chloride having an aluminum to chlorine ratio in the range of 5:1 to 6:1 which is the chlorination product of pseudoboehmite.

11. A method in accordance with claim 10 wherein the human skin to which the thixotropic aluminum hydroxide chloride is applied is the face or scalp.

12. A method of treating wounds or burns comprising topically applying over the wound or burn a bandage comprising an impregnated carrier in accordance with claim 5.

13. A method for providing heat treatment or cold treatment to body parts comprising heating or refrigerating a bandage comprising an impregnated carrier in accordance with claim 5 and applying said heated or refrigerated bandage to the body part to be treated.

14. An impregnated carrier in accordance with claim 5, wherein said aluminum hydroxide chloride is present in substantially the maximum amount which can be supported by the carrier.

15. An impregnated carrier in accordance with claim 5, wherein said aluminum hydroxide chloride is present in said carrier in an amount of 10-35 g/100 cm$^2$ of carrier.

16. An impregnated carrier in accordance with claims 5, 8, 14 or 15 wherein said carrier comprises polyurethane foam.

17. An impregnated carrier in accordance with claim 5, wherein said impregnant is present in said carrier in an amount of about 300 g/m$^2$.

* * * * *